(12) United States Patent
Kolappan

(10) Patent No.: US 11,525,113 B2
(45) Date of Patent: Dec. 13, 2022

(54) BIOREACTOR ASSEMBLY

(71) Applicant: GLOBAL LIFE SCIENCES SOLUTIONS USA LLC, Marlborough, MA (US)

(72) Inventor: Sankar Ganesh Kolappan, Karnataka (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 109 days.

(21) Appl. No.: 16/346,071

(22) PCT Filed: Oct. 26, 2017

(86) PCT No.: PCT/EP2017/077389
§ 371 (c)(1),
(2) Date: Apr. 29, 2019

(87) PCT Pub. No.: WO2018/077995
PCT Pub. Date: May 3, 2018

(65) Prior Publication Data
US 2019/0264157 A1    Aug. 29, 2019

(30) Foreign Application Priority Data
Oct. 31, 2016  (IN) ............................. 201611037205

(51) Int. Cl.
*C12M 3/00*      (2006.01)
*C12M 3/06*      (2006.01)
(Continued)

(52) U.S. Cl.
CPC ........... *C12M 27/16* (2013.01); *B01F 31/201* (2022.01); *B01F 31/23* (2022.01); *C12M 23/04* (2013.01);
(Continued)

(58) Field of Classification Search
CPC .............. B01F 11/0008; B01F 11/0017; B01F 2215/0073; C12M 23/04; C12M 23/48; C12M 27/16; C12M 41/42
See application file for complete search history.

(56) References Cited

U.S. PATENT DOCUMENTS 5,423,603 A * 6/1995 Reynolds ............ B01F 11/0008
366/208
6,190,913 B1    2/2001 Singh
(Continued)

FOREIGN PATENT DOCUMENTS

CN    202187007 U    4/2012
CN    204981893 U    1/2016
(Continued)

OTHER PUBLICATIONS

International Search Report as cited in International Application No. PCT/EP2017/077389 dated Jan. 23, 2018.
(Continued)

*Primary Examiner* — Liban M Hassan
(74) *Attorney, Agent, or Firm* — Jeff B. Vockrodt; Culhane Meadows, PLLC

(57) ABSTRACT

The present invention relates to a bioreactor assembly comprising
a plurality of trays (30) for holding a cell culture bag,
a holder (2) on which the trays are mounted side by side to form a first series of trays
rocking mechanism (4) for rocking the trays, the rocking mechanism (4) being operatively connected to each of the trays (30).
The invention also relates to a bioreactor system (100) comprising at least one bioreactor assembly.

4 Claims, 2 Drawing Sheets

Figure 1:
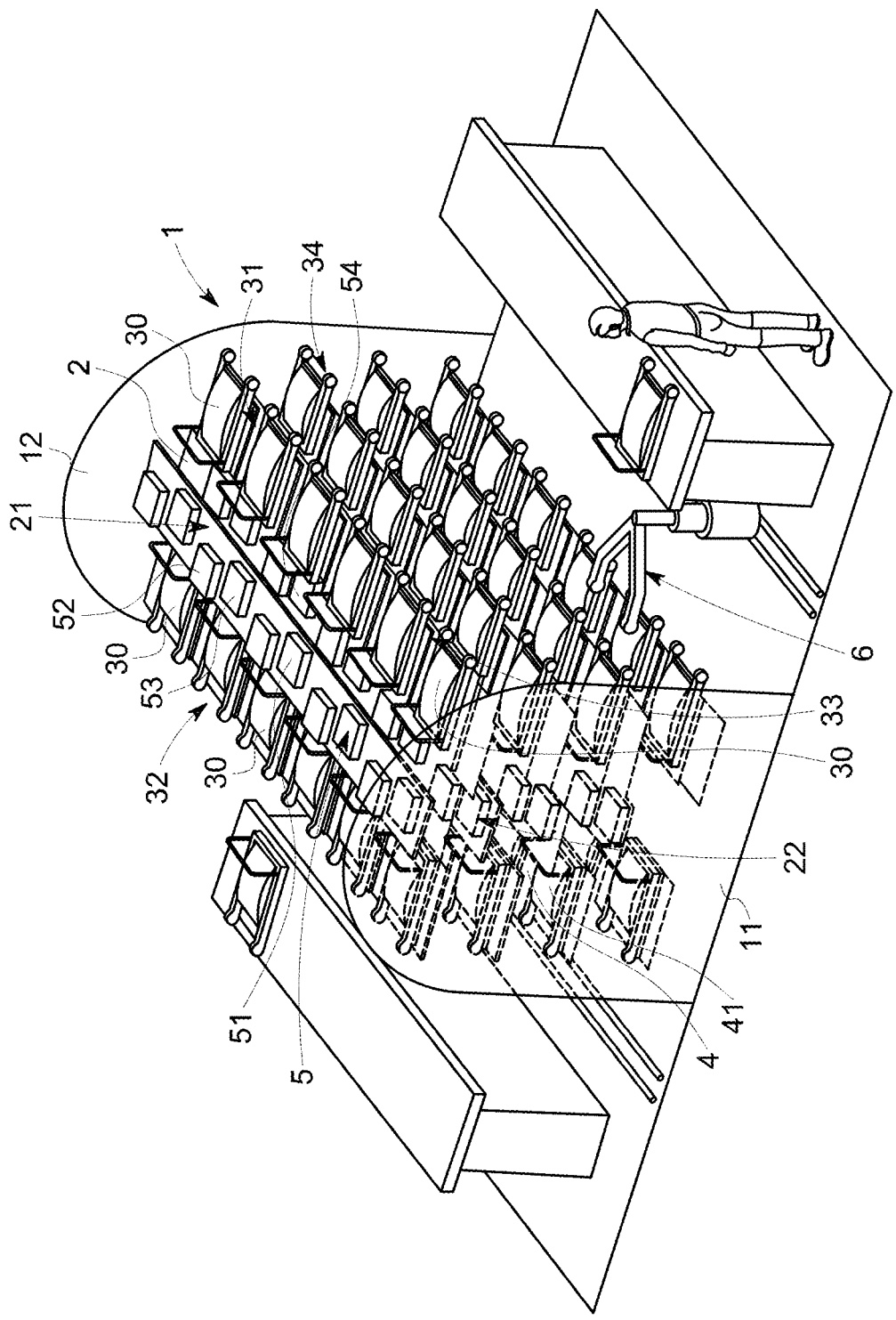

(51) Int. Cl.
  *C12M 1/12* (2006.01)
  *C12M 1/34* (2006.01)
  *B01F 31/23* (2022.01)
  *B01F 31/20* (2022.01)
  *B01F 101/44* (2022.01)

(52) U.S. Cl.
  CPC ............ *C12M 23/48* (2013.01); *C12M 41/42* (2013.01); *B01F 2101/44* (2022.01)

(56) References Cited

U.S. PATENT DOCUMENTS

| | | | |
|---|---|---|---|
| 2002/0155595 A1 | 10/2002 | Adelberg | |
| 2003/0040104 A1 | 2/2003 | Barbera-Guillem | |
| 2004/0209346 A1* | 10/2004 | Adelberg | ................ C12N 5/04 435/284.1 |
| 2006/0035368 A1 | 2/2006 | Malinge | |
| 2007/0026988 A1 | 11/2007 | Houtzager et al. | |
| 2008/0090288 A1* | 4/2008 | Hibino | ................... C12M 33/20 435/307.1 |
| 2008/0160597 A1* | 7/2008 | van der Heiden | ..... C12M 35/04 435/252.8 |
| 2012/0258441 A1 | 10/2012 | Gebauer et al. | |
| 2013/0316446 A1 | 11/2013 | Andersson et al. | |
| 2015/0093829 A1* | 4/2015 | Swanda | ................ C12M 23/22 435/420 |
| 2018/0002655 A1 | 1/2018 | Patil et al. | |
| 2018/0017988 A1 | 1/2018 | Kommrusch et al. | |

FOREIGN PATENT DOCUMENTS

| | | | | |
|---|---|---|---|---|
| CN | 113736655 A | 12/2021 | | |
| EP | 1944359 A1 | 7/2008 | | |
| JP | 2005168384 A | 6/2005 | | |
| JP | 2008513034 A | 5/2008 | | |
| JP | 2014506479 A | 3/2014 | | |
| JP | 2019522858 A | 8/2019 | | |
| WO | 2005111192 A1 | 11/2005 | | |
| WO | 2012/000502 A1 | 1/2012 | | |
| WO | WO-2012000502 A1 * | 1/2012 | ............ | C12M 23/14 |
| WO | 2012115581 A1 | 8/2012 | | |
| WO | 2016/113369 A1 | 7/2016 | | |
| WO | 2016/124505 A1 | 8/2016 | | |

OTHER PUBLICATIONS

Office Action received in Japanese Application No. 2019-522858 dated Aug. 10, 2021, with translation, 8 pages.
Office Action received in Chinese Application No. 201780067800.7 dated Apr. 13, 2022, with translation, 19 pages.

* cited by examiner

BIOREACTOR ASSEMBLY

CROSS-REFERENCE TO RELATED APPLICATIONS

This application is a 35 U.S.C. 371 National Phase of PCT Application No. PCT/EP2017/077389, filed on Oct. 26, 2017, which claims priority to IN Application No. 201611037205 filed Oct. 31, 2016, the disclosures of each of which are hereby incorporated by reference in their entirety.

TECHNICAL FIELD

The present invention relates to a bioreactor assembly for cell manufacturing. The invention also relates to a bioreactor system comprising at least one such bioreactor assembly.

BACKGROUND

The use of bioreactors for cultivation of cell samples is well known within the art, for instance through US2007/0269888 (Houtzager et al.) and U.S. Pat. No. 6,190,913 (Singh). In some embodiments, large batches are grown in fermentation vessels with capability for many liters of fluid, but in many cases it is more desirable to have a number of smaller samples in individual bags of only a few liters or less. Each bag generally needs access to nutrients, removal of waste products, and to be subjected to movements through stirring or rocking in order to allow the nutrients and air to mix with the cell sample.

The document US2007/0269888 (Houtzager et al.) mentioned above discloses one such bioreactor, comprising a plurality of cell samples in individual bags that are mounted in a reactor frame. The bags are kept in individual trays that are connected through a system of cooperating links in order to rock the bags.

One problem associated with the known bioreactors is that they are generally not able to handle large quantities of bags with sufficient monitoring and treatment to achieve the desired cell cultivation, and that they also take up large space. There is therefore a need for an improved bioreactor.

SUMMARY OF THE INVENTION

An object of the present invention is to eliminate or at least to minimize the problems mentioned above. The inventors have addressed these problems by devising a bioreactor, wherein a series of trays are arranged in connection with a holder. Thereby, a large number of cell culture bags can be cultivated simultaneously and in a space efficient way.

According to an aspect of the invention, the rocking mechanism comprises at least one motor, the motor being arranged to rock the trays by rotating or moving the holder. Thereby, the trays can be rocked in a simple and efficient way, generating the rocking required to facilitate cultivation of cells.

According to another aspect of the invention, the rocking mechanism comprise at least one motor and a plurality of rocking units operatively connected to said at least one motor, each rocking unit being arranged in connection with a tray, and wherein the rocking mechanism are configured to rock the trays by each rocking unit being driven by the motor to create a rocking motion such that each rocking unit is driven to rock one or more of said trays directly. Thereby, the holder can remain stationary and each tray can be rocked individually, allowing for the rocking of each tray to be determined based on the requirements of the specific cell culture bag placed in the tray.

According to yet another aspect of the invention, the assembly further comprises a control unit that is arranged to control the rocking mechanism, and that is preferably arranged to receive input signals from a plurality of interaction units and to transmit output signals to said interaction units. The interaction units can comprise a supply unit for supplying nutrients to cell culture bags placed in the trays and a waste unit for removing waste products from the cell culture bags, wherein the supply unit and the waste unit are driven by at least one pump for pumping nutrients and waste products to and from the cell culture bags via tubes. Thereby, the cell culture bags in the trays can be supplied with nutrients and have waste products removed, and this supply and removal can be controlled by the control unit, as well as the rocking of the trays. This allows for improving the cultivation of cells in the bioreactor assembly.

According to a further aspect of the invention, the bioreactor assembly further comprises a holding area for holding the interaction units and/or the control unit, said holding area being arranged at the holder. Thereby, the interaction units can be held in close vicinity to the cell culture bags, further reducing the space needed for the bioreactor assembly. Preferably, the control unit can monitor the contents of the cell culture bags and also store and/or transmit data regarding said contents to a user, either locally at the bioreactor assembly or at a distance.

According to yet another aspect of the invention, at least one of the trays is removably arranged. Thereby, that tray can be disconnected from the bioreactor assembly and accessed by an operator or an automated processing system for further handling the cell culture bag. Preferably, remover are provided for performing the disconnection and delivering the tray to a predetermined place, to facilitate handling of the tray in large bioreactor assemblies where it would be difficult for a human operator to access every tray manually. Of course, the removable arrangement also serves to allow for an addition of a new cell culture bag and the connection of that cell culture bag to the bioreactor assembly, so that a replacement of the contents of a tray is facilitated.

According to a further aspect of the invention, at least one of the trays is configured to be disconnected from the rocking mechanism. Thereby, the rocking of an individual tray can be stopped, to allow for removal/replacement or other handling, monitoring or testing, while the remaining trays can be allowed to continue rocking. This is especially advantageous in allowing the cultivation to continue even during removal, replacement, loading or emptying of the bioreactor assembly, and serves to shorten the cultivation time for the cell samples in the cell culture bags.

According to yet another aspect of the invention, the bioreactor assembly further comprises a second series of trays that are mounted on the holder opposite to the first series of trays and that are also operatively connected to the rocking mechanism. Preferably, the holder and the trays form a layer in the bioreactor assembly, and wherein the bioreactor assembly comprises at least one further such layer. Thereby, the number of trays and thereby the number of cell culture bags that can be cultivated simultaneously is further increased.

According to a further aspect of the invention, the plurality of trays are joined edge on edge to form a string of rocking trays. Thereby, the bioreactor assembly can be made with increased space efficiency and still reliably hold a large number of cell culture bags for cultivation.

The invention also comprises a bioreactor system according to the appended independent claim, having at least one bioreactor assembly as described above and also comprising a control unit for controlling the operation of the bioreactor assembly, interaction units, comprising a supply unit for providing a supply of nutrients to the cell culture bags and a waste unit for removing waste products from the cell culture bags, said supply unit and waste unit being arranged to be connected to each cell culture bag via tubes and each of the interaction units being driven by at least one pump, input for providing input to the system, and output for providing output from the system, wherein the control unit is operatively connected to the input, the rocking mechanism and each of the interaction units and to the output, and wherein the control unit is configured to control the operation of the rocking mechanism and the interaction units and to provide output signals for the output.

According to one aspect of the invention, the control unit is configured receive data regarding at least one property of the cell culture bags, and optionally to store said data and transmit it to said output. Thereby, the cultivation of cells in the cell culture bags can be monitored and data regarding them can be stored, displayed and/or transmitted to external units or presented to a user of the system.

Many additional benefits and advantages of the invention will become readily apparent to the person skilled in the art in view of the detailed description below.

DRAWINGS

Figure 2:
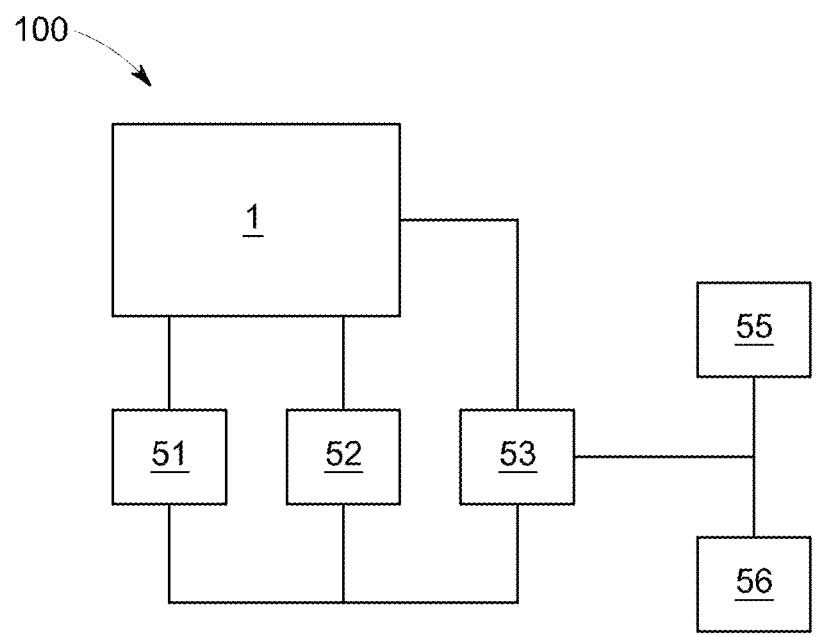

The invention will now be described in more detail with reference to the appended drawings, wherein FIG. 1 discloses a perspective view of a preferred embodiment of a bioreactor assembly according to the present invention;

FIG. 2 discloses a schematic view of a bioreactor system comprising at least one bioreactor assembly according to the invention.

DETAILED DESCRIPTION

FIG. 1 discloses a bioreactor assembly 1 according to a preferred embodiment of the present invention. The bioreactor assembly comprises a holder 2 that extends from a first end 11 to a second end 12 of the bioreactor assembly 1, and along which a first series of trays 31 is arranged. The first series of trays 31 comprises a plurality of individual trays 30 that are arranged along the holder 2 side by side and that are each operatively connected to the holder 2. This means that the trays 30 are arranged in parallel to form the series. Also included in the bioreactor assembly 1 is a rocking mechanism 4, preferably in the form of at least one motor 41 that may be arranged along the holder 2 or at one end of the bioreactor assembly 1 to rock the trays together, or alternatively at another suitable location in or at the bioreactor assembly 1.

The rocking mechanism 4 are operatively connected to each of the trays 30 and arranged to generate a rocking motion for each tray 30 so that contents of a cell culture bag (not shown) placed in the tray 30 are kept moving, in order to improve distribution of nutrients, removal of waste products, to aid in cell expansion. The rocking mechanism 4 can be connected through the holder 2 or directly to each tray 30, depending on what is suitable for a specific embodiment of the invention.

When the rocking mechanism 4 is connected through the holder 2, the trays can be rocked by rotating the holder alternately in a clockwise and an anti-clockwise direction. Alternatively, the holder 2 can be moved or rocked from side to side. The rocking mechanism 4 can comprise a crank on one end of the holder 2, wherein the crank is driven by the motor 41 to rotate the holder 2 back and forth to make the trays 30 rock together on the holder.

When the rocking mechanism 4 are connected to each tray 30 individually, the rocking mechanism 4 may comprise a plurality of rocking units (not shown) that are operatively connected to said at least one motor, each rocking unit being arranged in connection with a tray, and the rocking mechanism can be configured to rock the trays by each rocking unit being driven by the motor to create a rocking motion. Thus, the rocking mechanism 4 is connected to the rocking units such that each rocking unit is driven to rock one or more of said trays directly. The rocking mechanism 4 can comprise multiple cams on a common shaft, the cams and shaft being driven by the motor 41 to rock each of the trays 30 individually.

The rocking motion generated for a tray 30 is preferably an angular motion about a pivot point or a four-bar linkage motion.

In an alternative embodiment, the individual trays 30 can be joined edge on edge to form a string of rocking trays that is able to hold a plurality of cell culture bags. The string of rocking trays is mounted similarly to the individual trays 30 and is rocked in essentially the same way, but will not require a plurality of rocking units.

In the preferred embodiment, a second series of trays 32 are also arranged along the holder 2 in essentially the same distribution as the first series of trays 31 mentioned above. Together, the first and second series of trays 31, 32 and the holder 2 form a layer of trays 33 where each individual tray 30 is on substantially the same height above a floor on which the bioreactor assembly 1 stands. The rocking mechanism 4 is preferably connected in the same way to each tray 30, regardless of to which series the tray 30 belongs.

Thus, the rocking mechanism 4 preferably include at least one motor and either individual rocking units placed in connection with each tray 30 or a rocking device for the holder 2, where the rocking device is arranged to create the rotational movement or the rocking movement of the holder 2. The rocking mechanism 4 also comprise a connection between the motor or motors and the rocking units or rocking device, to allow the motor to drive the rocking motion of the trays 30.

In order to further increase the number of trays available, at least one but preferably two or more further layers of trays 34 are preferably provided in the bioreactor assembly 1. This way, a multilayered bioreactor assembly 1 is created. Thereby, a large number of trays 30 can be provided in a very space efficient way, allowing for the cultivation of a very large number of cell culture bags simultaneously.

Preferably, at least one storage area 5 is provided in connection with the holder 2 and configured to hold at least one but preferably a plurality of interaction units that serve and monitor the cell culture bags in the trays 30. The storage area 5 is preferably in the form of a static shelf 5. These interaction units include a supply unit that is arranged to hold a supply of nutrients, generally in the form of Meida, air mixout (oxygen, $CO_2$, $N_2$), and a waste unit that is arranged to receive a waste product from the cell culture bags. The supply unit and waste unit are preferably connected to each cell culture bag in the trays 30 via tubes that run along the holder 2 and extend to each tray, ending in connectors for easy connection to the cell culture bags, and at least one pump 54 that pumps the nutrients to the cell culture bags and at least one pump 54 that pumps the waste products from the cell culture bags.

The interaction units can comprise one large unit for each type of interaction unit placed in the bioreactor assembly 1, but may optionally comprise a plurality of interaction units of each type, mounted on each layer 33, 34 in connection with each holder 21, 22, to have easy access to the cell culture bags in the trays 30 on each layer 33, 34. The number of pumps 54 may vary depending on this.

Also included among the interaction units is at least one control unit 53 that is arranged to monitor at least one property of the cell culture bags in the trays 30. That property may be the concentration or amount of a substance in the cell culture bag, the supply rate of nutrient or removal rate of waste, the temperature in the cell culture bag, or any other property connected with the cultivation of cells in the cell culture bags. The control unit 53 is operatively connected to each cell culture bag and may also store and/or process collected data that corresponds to said property or properties. Data may also be displayed at the bioreactor assembly 1 or remotely on a separate unit, and may also be configured to receive input from a control unit or from a human operator and to alter its operation depending on that input. The control unit 53 may also be configured to control the operation of the other interaction units, such as the supply unit 51, waste unit 52, and pumps 54 to and from these units.

The trays 30 are preferably arranged to be removable from the bioreactor assembly 1, so that the individual tray 30 can be disconnected from the holder 2 and taken out of the bioreactor assembly 1. This removal can be made by a human operator but is preferably automated and performed by a remover 6 in the form of a robot or similar that serves to disconnect the interaction units from the cell culture bag and the tray 30 from the holder 2. The tray 30 can then be taken to a desired location, either to a human operator or to an automated system for removal of the cell culture bag and/or placement of a new cell culture bag in the tray 30 before reinsertion into the bioreactor assembly 1. Preferably, the rocking mechanism can be disconnected from each tray 30 individually, so that the remaining trays 30 in the bioreactor assembly can continue rocking while one tray 30 is removed and reinserted.

The trays 30 can be mounted on the holder 2 by any suitable connection, such as a slide and lock mechanism or other mechanism that can hold the tray 30 robustly with the holder 2, either directly or via a rocking unit as described above.

The bioreactor assembly 1 forms a bioreactor system 100 together with the interaction units mentioned above, namely the supply unit 51, the waste unit 52 and the control unit 53, as shown schematically by FIG. 2. The control unit 53 is configured to interact with the bioreactor assembly 1 in order to control the rocking mechanism 4 and the removal of trays 30, but also with the supply unit 51 and the waste unit 52 and any further units provided, such as an air mixout unit for instance. Input 55 are provided for giving input data to the control unit 53, as well as output 56 that are provided for receiving output data from the control unit 53 and transmitting or displaying such data. The control unit may also be configured to store and/or process data, or alternatively such processing and storage can be performed at a remote unit that is configured to receive data from the output 56. The input 55 may be any device suitable for an operator or a separate control system to interact with the control unit 53 in order to give input signals. Thus, the input 55 may be a computer, a keyboard, a computer screen or any other suitable device. Similarly, the output 56 may be in the form of a display or a computer, or simply in the form of a transmitter for transmitting signals from the system 100. It is also to be noted that the input 55 and/or output 56 may be integrated with the control unit 53.

It is to be noted that any features described above with reference to one embodiment or suitable mode of operation for the bioreactor assembly 1 and bioreactor system 100 may freely be combined with other features of the present invention, unless such a combination is clearly stated as unsuitable herein.

The invention claimed is:

1. A bioreactor assembly comprising:
   a plurality of trays configured to hold a plurality of cell culture bags,
   a holder on which the trays are removably mounted side by side to form a first series of trays of the plurality of trays on a first side of the bioreactor assembly and a second series of trays of the plurality of trays on a second side of the bioreactor assembly opposite the first side;
   a rocking mechanism that is operatively connected to the first series of trays and second series of trays and configured to rock the trays on each side of the bioreactor assembly, wherein the rocking mechanism comprises at least one motor operatively connected to one or more trays and configured to rock the trays; and
   at least one control unit, said at least one control unit is positioned above a holding area of the holder central to the first series of trays and second series of trays and is arranged to control the rocking mechanism;
   wherein the plurality of trays are configured to be disconnected from the rocking mechanism such that the rocking of an individual tray of the plurality of trays is stopped while the remining trays are permitted to continue rocking.

2. The bioreactor assembly according to claim 1, wherein at least one of the trays is configured to be removable from the bioreactor assembly.

3. The bioreactor assembly according to claim 2, further comprising a remover for removing the tray from the bioreactor assembly.

4. The bioreactor assembly according to claim 1, wherein the individual tray after stopping may be removed and/or replaced.

* * * * *